United States Patent [19]

Comerford et al.

[11] 3,952,347

[45] Apr. 27, 1976

[54] BIODEGRADABLE BARRIER FILM AND ABSORBENT PAD UTILIZING SAME

[75] Inventors: John M. Comerford, Morganville; Chandra Kapur, East Brunswick, both of N.J.

[73] Assignee: Personal Products Company, Milltown, N.J.

[22] Filed: Dec. 13, 1973

[21] Appl. No.: 424,404

[52] U.S. Cl. .......................................... 5/335; 5/91; 5/334 R; 5/345 R; 5/355; 5/361 R; 128/284; 128/285; 128/287; 128/290 R; 128/296; 260/8; 260/17.4 ST; 260/DIG. 43; 428/212; 428/532; 428/533; 428/913

[51] Int. Cl.² .................... A61F 13/00; A61G 7/04; C08L 3/02; C08L 89/00

[58] Field of Search .................. 260/8, 17.4 ST; 428/212, 532, 533, 913; 5/91, 334 R, 345 R, 355, 361 R; 128/284, 285, 290 R, 296, 287

[56] References Cited
UNITED STATES PATENTS

| | | | |
|---|---|---|---|
| 3,187,747 | 6/1965 | Burgeni et al. ................... | 128/156 |
| 3,616,797 | 11/1971 | Champaigne ..................... | 128/284 |
| 3,645,836 | 2/1972 | Torr .................................. | 128/284 |
| 3,658,062 | 4/1972 | Kapur ............................... | 128/287 |
| 3,683,917 | 8/1972 | Comerford ........................ | 128/287 |
| 3,800,797 | 4/1974 | Tunc ................................. | 128/290 |
| 3,871,037 | 3/1975 | Willington ............................ | 5/91 |

*Primary Examiner*—Donald E. Czaja
*Assistant Examiner*—Edward Woodberry
*Attorney, Agent, or Firm*—J. Lipow

[57] ABSTRACT

A biodegradable barrier film is provided which is useful as a barrier layer in absorbent pads such as sanitary napkins and diapers. The film comprises a matrix of a non-biodegradable film-forming material which is resistant to solubility in water having a biodegradable material homogeneously dispersed therein, the biodegradable material being present in said film in an amount from about 40 to about 60 weight percent based on the total weight of said biodegradable and said non-biodegradable film-forming material in said film.

13 Claims, No Drawings

BIODEGRADABLE BARRIER FILM AND ABSORBENT PAD UTILIZING SAME

BACKGROUND OF THE INVENTION

This invention relates to a biodegradable barrier film and to disposable absorbent pads, such as sanitary napkins or diapers, for absorbing and retaining body fluids and exudates and utilizing the biodegradable barrier film to prevent the spread of said body fluids.

Disposable absorbent products, such as sanitary napkins, comprise a fibrous body of one or more layers of highly absorbent fibers, usually wrapped within a fluid-permeable cover which may comprise a woven or nonwoven fabric. In addition, such products usually contain a fluid impervious barrier layer to prevent the spread of the menstrual, or other body fluid to the clothing of the wearer.

Both the fibrous body and the fluid-permeable cover are usually cellulosic in nature and are therefore biodegradable and capable of decomposition within a conventional sewage disposal system. The fluid impervious barrier on the other hand is usually made of a water-repellent synthetic polymer, such as polyethylene, which is non-biodegradable and retains its structural integrity even after prolonged exposure to the sewage disposal process. Undegraded plastic film barriers in a sewage system impede the free flow of sewage fluids and impair the functioning of the system.

To provide the desired biodegradability in sanitary napkins, diapers and other disposable absorbent products, it has been proposed to make the barrier films for these products out of biodegradable materials. U.S. Pat. No. 3,602,225 of Edward A. Wielicki, teaches the use of barrier films made of plasticized regenerated cellulose films. My U.S. Pat. No. 3,683,917, teaches the use of barrier films comprising a cellulosic tissue material treated with a water-repellent material. Barrier films made of biodegradable materials have not been used extensively because of their expense and because of the limited range of properties available in such films.

In accordance with one aspect of the present invention, a biodegradable barrier film which comprises a biodegradable material homogeneously dispersed in a matrix of a non-biodegradable film-forming material which is resistant to solubility in water, the biodegradable material being present in said film material in an amount from about 40 to about 60 percent by weight based on the total weight of said biodegradable and said non-biodegradable film-forming material in said film. A plasticizer is preferably incorporated into the film in amounts up to 60 percent by weight based on the entire weight of the film.

The barrier film is impervious to fluid discharge by reason of the film-forming matrix material which is resistant to solubility in water. In barrier films intended for diapers, and in other applications in which the barrier film is likely to come into contact with a relatively large volume of a highly fluent discharge, the film-forming material is preferably a water-insoluble material capable of forming a coherent self-supporting film.

In barrier films intended for sanitary napkins, and in other applications in which the barrier film is likely to come into contact with a smaller volume of a less fluent, or mucilaginous discharge, the film material need not be water-insoluble but can be slowly soluble in water provided it is in a self-supporting film of sufficient thickness to maintain its integrity during the functioning of the absorbent pad. Suitable film-forming materials include polyethylene, polypropylene, polyethylene terephthalate, polyvinyl chloride, high molecular weight polyvinyl pyrrolidone and polyvinyl alcohol.

The biodegradable material used in the barrier film of this invention is a finely divided material which is preferably a material which swells in water. Suitable biodegradable materials include carbohydrates such as starch, finely divided regenerated cellulose, starch dextrin and natural gums, such as gum acacia and gum tragacanth; natural resins, such as rosin; proteins such as collagen; and alginates.

When the biodegradable and non-biodegradable materials are present in the film of this invention in the proportions described herein, the film functions as a barrier to body discharge fluids with the essential physical properties of the non-biodegradable film-forming material includes effective resistance to the passage therethrough of the fluids. The film is, however, degradable in sewage systems within the time that sewage is usually treated in such systems, as now to be explained. Without being bound to any theory of operation, it is believed that the biodegradable material is degraded by the action of bacteria in the sewage system and that this degradation is of a continuous character and continues until it creates weakened portions, and ultimately voids the structure of the film. In time the degraded film can no longer maintain its integrity and it breaks down into many pieces, small enough to be handled by normal sewage systems. When the proportion of biodegradable material is in excess of the specified range, the amount of film-forming material is insufficient to provide the necessary strength and other physical properties required in the film of the invention. Conversely, when the proportion of biodegradable material is below the specified range, the breakdown of the film will not be fast enough and/or extensive enough to provide the disintegration of the film into the small particles required for handling by the sewage system.

The films of the invention may be prepared by various methods, depending on the nature of the non-biodegradable film-forming material. A preferred method of preparing the barrier film of the invention when the film-forming material is polyvinyl alcohol is by casting the film from an aqueous dispersion of film-forming material, biodegradable material and plasticizer and then driving off the water. The thickness of the film suitable for use in this invention is dependent on the nature of the materials used. The films should be thick enough to provide the necessary strength and water barrier and should be thin enough to provide the necessary flexibility and to avoid unnecessary expense. The films generally range from about one to two mils in thickness but may be as thin as ½ mil, or as thick as about 4 mils, if desired.

EXAMPLE

In a specific embodiment of this invention, 30 parts of potatoe starch dextrin is mixed with 900 parts of cold water to form a slurry. Fifty parts of polyvinyl alcohol (99% hydrolyzed) and 20 parts of glycerol are added to the slurry with continued stirring. The resulting dispersion is then heated to 200°F. and stirred at that temperature for 30 minutes.

The heated dispersion is then poured onto a smooth glass plate covered with a light film of carnauba wax to form a film layer which is then dried in an oven at 160°F. for five to ten minutes. The film layer is peeled off and comprises a self-supporting film about 1½ mils in thickness having sufficient strength, flexibility and water-imperviousness to serve as a moisture barrier layer in a sanitary napkin or diaper.

The effectiveness of the film as a moisture barrier may be tested by the test described in the aforementioned U.S. Pat. No. 3,683,917 at column 2, lines 39 to 67 and column 3, lines 1 to 22.

The susceptibility of the film to decomposition under anaerobic digestion conditions is tested as follows:

A first series of laboratory digesters are set up, each containing approximately one liter of a mixture of digested sewage solids, ripe sludge, and various concentrations of the products submitted for degradation studies. The mixtures are maintained at a constant temperature of 28°C. until completely digested. One of the digestors, without product, serves as a control. To each of the others, is added a measured amount of the material to be tested. A second series of digestors are set up in the same manner as above but designed to follow the course of digestion without inhibiting gas collection. Gas evolved from the second series of the digestion mixtures is collected and the volume is measured daily until gas production from all digestors in this series has come to a halt. At the end of the digestion, the contents of all the digestors of each series are analyzed for various constituents. In addition, samples are withdrawn on a weekly basis from the first series and analyzed for volatile acids, pH, degree of digestability and total solids content. A comparison with the original organic solids content of the original sludge provides an index of the extent to which the material has been destroyed. Likewise, the daily gas production values gives indications of the decomposition rates and the total volatile matter destroyed.

In tests of the type described above, the films of this invention are generally destroyed to a substantial extent, of the order of about 50 percent, or more, when the components of the film are within the ranges specified above.

The films of this invention may be prepared by methods other than the method described above. They may be cast, for example, from organic solvents or dispersion media instead of from aqueous systems. Alternatively, the films may be extruded by conventional extrusion procedures from a mixture of the film components in the desired proportions with intimate admixture being achieved during the extrusion. The extrusion method is preferred when the non-biodegradable film-forming material is a material, such as polyethylene, which is not readily soluble at high concentrations in most solvents and which is usually fabricated in film form by extrusion.

As stated above, the essential components of the film of this invention are the non-biodegradable film-forming material, and the biodegradable material with the biodegradable material comprising from about 40 to about 60 percent by weight based on the total weight of these two materials in the film. When a plasticizer is present, it can be used in amounts up to about 60 percent by weight based on the entire weight of the film. Preferably, the non-biodegradable film-forming material and the biodegradable material are each present in amounts from about 38 to about 45 percent by weight and the plasticizer is present in an amount from about 10 to about 25 percent, all based on the total weight of the material. Other additives, such as pigments or stabilizers may be present in the film in amounts up to about 15% by weight.

In the example described above, glycerol was used as the plasticizer. It is to be understood, however, that other materials may be used, the selection being dependent on the nature of the non-biodegradable film-forming material. Where the non-biodegradable film-forming material is polyvinyl alcohol, other plasticizers include polyols such as ethylene glycol, diethylene glycol, 1,2 propanediol, 1,3 butanediol, 1,4 butanediol, 2,3 butanediol, polyethylene glycols, polypropylene glycols, and block copolymers of oxyethylene and oxypropylene units. For other film-forming materials other plasticizers may be used which are known to be compatible with the film-forming materials. Typical plasticizers include high boiling relatively non-volatile liquid esters such as butyl stearate, butoxyethyl stearate, methoxyethyl oleate, methyl abietate, diethyl phthalate, dibutyl phthalate, triphenyl phosphate, tricresyl phosphate, dibutyl sebacate, and ethylene glycol diabetate.

The film of this invention may be used as a moisture barrier in absorbent structures such as sanitary napkins, disposable diapers, surgical dressings, underpads, compresses and the like.

Disposable sanitary napkins are commonly made of a fibrous body or core of one or more layers of highly absorbent fibers wrapped within a soft, fluid permeable cover with a barrier film within the wrapper at one side thereof. A suitable disposable sanitary napkin structure is described in my above-cited U.S. Pat. No. 3,683,917, which is incorporated herein by reference, the barrier film of this invention being substitutable for the barrier film disclosed in said patent.

Disposable diapers are commonly made of a fibrous, highly absorbent batt, having a facing layer on one face thereof of lesser wettability than the absorbent batt and having on its opposite face a water-impervious layer. A suitable disposable diaper structure is described in Mesek et al., U.S. Pat. No. 3,683,916, which is incorporated herein by reference, the barrier film of this invention being substitutable for the impervious layer disclosed in said patent.

It will be understood by those skilled in the art that other variations and modifications may be employed without departing from the scope of the invention as defined in the appended claims.

What is claimed is:

1. A biodegradable barrier film comprising a matrix of a non-biodegradable film-forming material which is resistant to solubility in water having a biodegradable material homogeneously dispersed therein, said biodegradable material being present in said film in an amount from about 40 to about 60 percent by weight based on the total weight of said biodegradable material and said non-biodegradable film-forming material in said film, said film resisting the passage of body discharge fluids therethrough.

2. A biodegradable barrier film in accordance with claim 1 and also containing a plasticizer in an amount not more than 60 weight percent based on the entire weight of the film.

3. A biodegradable barrier film in accordance with claim 1 in which said biodegradable material and said non-biodegradable material are each present in amounts from about 38 to about 45 percent by weight based on the entire weight of the film.

4. A biodegradable barrier film in accordance with claim 1 wherein said biodegradable material is a carbohydrate.

5. A biodegradable barrier film in accordance with claim 4 wherein said carbohydrate is a starch.

6. A biodegradable barrier film in accordance with claim 4 wherein said carbohydrate is a dextrin.

7. A biodegradable barrier film in accordance with claim 1 wherein said biodegradable material is a protein.

8. A biodegradable barrier film in accordance with claim 6 wherein said protein is collagen.

9. A biodegradable barrier film in accordance with claim 1 wherein said non-biodegradable film-forming material is a water-insoluble polyvinyl alcohol.

10. A biodegradable barrier film in accordance with claim 1 wherein said non-biodegradable film-forming material is polyethylene.

11. A biodegradable barrier film comprising a matrix of a water-insoluble polyvinyl alcohol having homogenously dispersed therein a dextrin and a plasticizer, said dextrin being present in an amount from 40 to 60 percent by weight based on the total weight of dextrin and polyvinyl alcohol and said plasticizer being present in an amount from about 10 to about 75 percent by weight based on the entire weight of said film, said film resisting the passage of body discharge fluids therethrough.

12. In a disposable absorbent pad comprising a biodegradable absorbent filler material and a moisture barrier layer, the improvement which comprises utilizing as said barrier layer the biodegradable barrier film of claim 1.

13. The barrier film of claim 1 wherein said biodegradable material is a carbohydrate and said nonbiodegradable film forming material is polyvinyl alcohol.

* * * * *

Disclaimer 3,952,347.—*John M. Comerford*, Morganville and *Chandra Kapur*, East Brunswick, N.J. BIODEGRADABLE BARRIER FILM AND ABSORBENT PAD UTILIZING SAME. Patent dated Apr. 27, 1976. Disclaimer filed July 31, 1978, by the assignee, *Personal Products Company*.

Hereby enters this disclaimer to all claims of said patent.

[*Official Gazette October 24, 1978.*]